United States Patent
Rapp et al.

(10) Patent No.: US 6,314,791 B1
(45) Date of Patent: Nov. 13, 2001

(54) SURFACE ACOUSTIC WAVE SENSOR

(75) Inventors: Michael Rapp, Eppelheim; Achim Voigt, Linkenheim-Hochstetten, both of (DE)

(73) Assignee: Forschungszentrum Karlsruhe GmbH, Karlsruhen (DE)

( * ) Notice: Subject to any disclaimer, the term of this patent is extended or adjusted under 35 U.S.C. 154(b) by 0 days.

(21) Appl. No.: 09/511,686

(22) Filed: Feb. 23, 2000

Related U.S. Application Data

(63) Continuation-in-part of application No. PCT/EP98/06011, filed on Sep. 21, 1998.

(30) Foreign Application Priority Data

Oct. 20, 1997 (DE) ................................................ 198 46 261

(51) Int. Cl.[7] ............................ G01N 29/02; G01N 29/24

(52) U.S. Cl. ...................... 73/24.06; 73/31.06; 73/32 A; 73/54.41; 73/61.79; 310/313 B

(58) Field of Search ................................ 73/24.01, 24.05, 73/24.06, 31.05, 31.06, 32 A, 54.41, 61.79; 310/313 R, 313 B, 313 D

(56) References Cited

U.S. PATENT DOCUMENTS

| | | | |
|---|---|---|---|
| 3,921,093 | * 11/1975 | Lewis | ................................... 331/1 A |
| 5,076,094 | 12/1991 | Frye et al. | ........................... 73/19.03 |
| 5,117,146 | 5/1992 | Martin et al. . | |
| 5,661,226 | * 8/1997 | Bowers et al. | ...................... 73/24.01 |
| 5,918,258 | * 6/1999 | Bowers | ............................... 73/24.06 |

FOREIGN PATENT DOCUMENTS

| | | |
|---|---|---|
| 0 542 469 | 5/1993 | (EP) . |
| 0 618 446 | 10/1994 | (EP) . |
| 0 750 192 | 12/1996 | (EP) . |
| WO 93/07463 | 4/1993 | (WO) . |
| WO-99/ 21001-a1 | * 4/1999 | (WO) ................................ 73/24.01 |

* cited by examiner

Primary Examiner—Hezron Williams
Assistant Examiner—Rose M. Miller
(74) Attorney, Agent, or Firm—Klaus J. Bach

(57) ABSTRACT

In a sensor comprising a housing, through which a medium to be examined is conducted, the housing includes at least two passive building components capable of oscillating and oscillator circuits of which each includes an amplifier component and a variable phase shifting component providing for a phase shift range sufficiently large to switch the oscillating components off while the amplifier component remains operating.

7 Claims, 3 Drawing Sheets

SURFACE ACOUSTIC WAVE SENSOR

This is a continuation-in-part application of international application PCT/EP98/06011 filed Sep. 21, 1998 and claiming the priority of German application 197 46 261.8 filed Oct. 20, 1997.

BACKGROUND OF THE INVENTION

The invention relates to a surface acoustic wave sensor comprising at least two oscillating passive components having oscillator circuits as measuring oscillators disposed in a housing through which a medium to be tested is conducted.

Such a sensor is known for example from DE 44 17 170.

Modified acoustic surface wave—or Surface Acoustic Wave (SAW) building components can be employed for the chemical sensing of gases or liquids by applying a respective chemically reactive coating to the components. With the ab- and adsorption of the analyte, the mass of the coating as well as the elastic parameters thereof change, whereby the sound propagation speed of the surface wave changes. In order to measure the change of the sound propagation speed of a surface wave in a simple manner, it is common practice to include in an oscillator circuit a coated SAW component, which is used as a frequency determination element.

The sound propagation speed change results in a proportional change of the oscillator frequency, which can be determined with a good approximation and can be measured with a high resolution of typically $10^{-6}$. With an appropriate selection of sorption layers, almost any number of gaseous analytes can be examined with this technique. Of greatest interest are those materials for which qualitative and quantitative determinations are difficult to perform with other chemical microsensors. Those are organic solvents such as hydrocarbons (hexane octane, decane, various fuels), alcohols (methanol, ethanol, halogenized hydrocarbons (CKW's, FCKW's), and aromatics (benzene, toluene).

EP 0 509 328 A2 discloses an arrangement of 3 SAWs, which are arranged, however, in series. This results in different flow conditions in the individual sensors.

EP 0 477 684 A1 discloses an arrangement of more than 2 SAWs with different coating. The sensors are not arranged however in any particular way.

If several oscillators are operated in a small space at almost the same frequency, there is a cross-influence as a result of the electromagnetic transgressions. In an extreme case, this may result in a lock-in situation (oscillators vibrate at the same frequency). This behavior limits the possibilities of miniaturization of HF oscillators with similar frequencies. The problem can be circumvented if the oscillators are switched on and off. When switched on again, the oscillators drift because of thermal changes whereby the measuring sensitivity of for example a sensor is reduced. In order to avoid this, it would be necessary to wait after each switching on until a thermal equilibrium has been established. This however results in a long down time.

It is the object of the present invention to provide a sensor of the type described above, wherein, however, electromagnetic transgression of the oscillators is avoided without sensitivity losses and extended down times.

SUMMARY OF THE INVENTION

In a sensor comprising a housing including at least two passive building components capable of oscillating and oscillator circuits and with means for passing a medium to be examined through the housing, the oscillator circuits each include an amplifier and a variable phase shifting component providing for a phase shift range sufficiently large to switch the oscillating components off while the amplifier remains operating.

The particular advantage of the invention resides in the combination of damping-tolerant oscillators (high amplification of the active component) with adjustable phase (phase shifter by means of coil and capacity diodes) with the capability to switch the oscillators off. This eliminates the need for a separation of the sensor chambers since the oscillators can be multiplexed and operated at the same time at their optimal phase points.

This kind of switching potentially permits the miniaturization of sensor oscillator arrays (BAW (QMB), SAW, capacitive oscillator principles) and, by a selection of the optimal operating points of the oscillators (phase), provides at the same time for an increase in the sensitivity.

In front of the amplifier input and output of an oscillator, a phase shifter is arranged, which is electrically adjustable by way of capacity diodes. By applying a predetermined voltage the oscillator vibrates at a predetermined phase condition. This means that the arrangement can be adjusted to the phase point of the passive regenerative component, which is optimal for the particular purpose or to fully exit the transmission range of the passive component by totally de-tuning the phase shifter with the voltage applied thereto. The phase condition for the oscillation is then no longer fulfilled and it breaks off. The same "switching" behavior could be achieved by the use of PIN diodes.

A similar principle is utilized in connection with quartz-stabilized VCOs (Voltage-Controlled Oscillators). In that case, however, the phase is only shifted; the oscillator is not switched.

Below, an embodiment of the invention will be described on the basis of the accompanying drawings.

BRIEF DESCRIPTION OF THE DRAWINGS

FIG. 1 shows, in principle, a miniaturized sensor head utilizing separately controllable oscillators.

Figure 1:
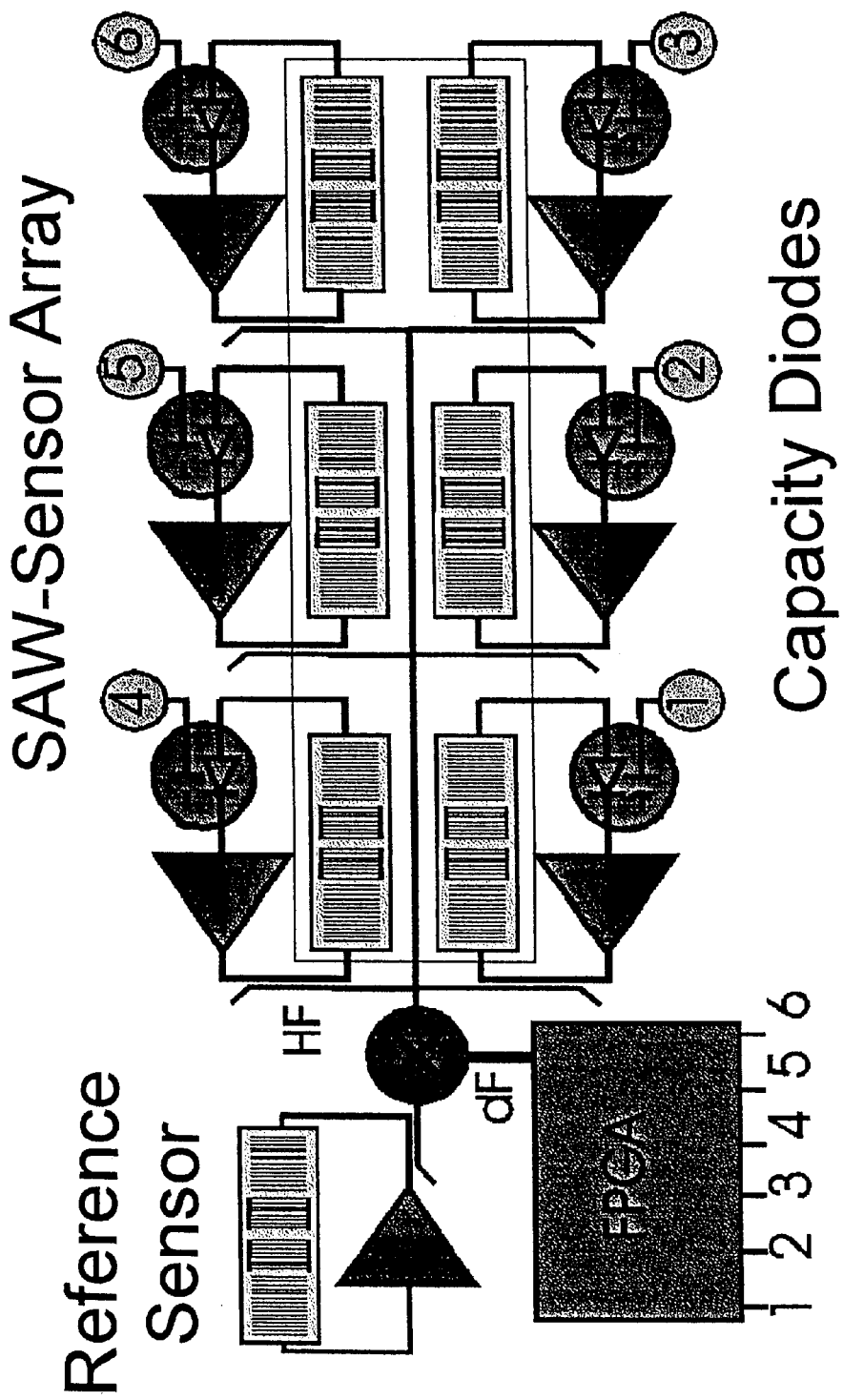
FIG. 1 shows a sensor arrangement in principle.

A micro-electronic circuit, in this case, a FPGA (free programmable gate array) provides at the outputs 1 . . . 6 the respective signals for controlling the capacity diodes of the six measuring oscillators, which each consist of SAWs and the oscillator circuit. Furthermore, it includes a fast connector timely synchronized with the respective channel. The particular HF signal of the respective active oscillator is mixed down with a permanently oscillating reference oscillator and the low frequency difference signal (dF) is supplied to the FPGA counter.

It is, for example, possible to measure the respective oscillation frequency of the SAW by an off-switching of the individual oscillators. The medium to be examined is supplied to the individual SAW by way of serial or parallel channels, which are not shown in the drawings.

Figure 2:
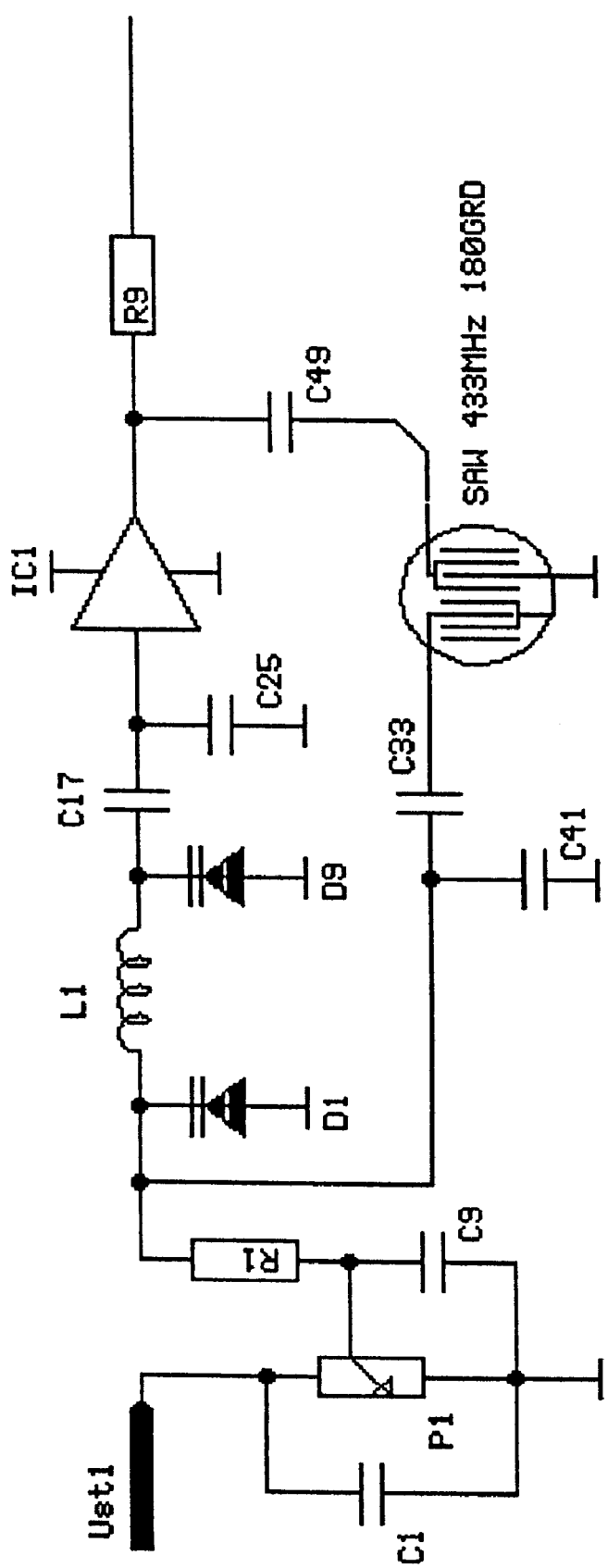
FIG. 2 shows an exemplary embodiment of an oscillator amplifier.

FIG. 2 shows a circuit arrangement for a prototype of a SAW array being developed.

It clearly shows the π phase shift network at the input of the respective oscillator amplifiers. By way of the potentiometer, the optimal phase of the oscillation circuit is adjusted and the respective oscillators are switched by on and off switching of the constant control voltage (Ust x).

In the circuit as shown in FIG. 2, the phase shifter in the present oscillator is in the form of a low pass LC-, PI-filter in which the center frequency is de-tuned by means of capacity diodes.

The phase shifter can be realized by means of pin diodes, PC, RL, LC members.

Switching is done on a high-, low-, all pass-, or resonance circuit.

C1, C9, R1 on P1 act at low pass and serve for the uncoupling of the high frequency of the oscillator with respect to the voltage input Ust1. The switching impulse for the on and off switching of the oscillator is applied to Ust1.

By means of the trimmer P1, the control voltage of the phase shifter consisting of the LC $\pi$-low pass D1, D9, L1, C41, C25 can be adjusted and, as a result, the phase position of the oscillator can be adjusted to the optimal sensitivity of the SAW sensor.

C17, C33 and C49 serve for the uncoupling of the DC voltage from the high frequency voltage.

By way of R9, the high frequency amplifier IC1 obtains its operating current. At the same time, the oscillator frequency is uncoupled by way of R9 in a high-ohmic manner.

Instead of the SAWs (433 Mhz, 180° phase) any other frequency determining passive component (for example a vibration quartz, 0° phase position) or LC member may be utilized. In that case, another amplifier must be selected for the IC1. The amplifier must be adapted in its phase position to the passive components in the feedback branch in order to ensure the phase conditions for the oscillation in the adjustment area of the phase shifter.

In the present sensor head, eight sensors are multiplexed one after the other, and the individual high frequencies are mixed down by the continuously oscillating reference sensor.

The relatively low frequency mixed frequencies can then be further processed by a fast digital counter, for example, a reciprocal counter.

With this arrangement of switched oscillators, the sensors can be arranged in a spatially tight manner, whereby a miniaturization of the sensor arrangement can be achieved. This also permits to minimize the measuring volume, which is an important advantage for many applications in the chemical analysis.

By supplying samples to the sensors serially, the measuring volume can be further reduced under the same gas flow conditions since the same gas flow reaches all the sensors in the sensor head. The sensor signals however, are slightly displaced time-wise because of the flow speeds and the sampling line length, but this is only a small disadvantage. (In the present embodiment, there is a time difference of 1 sec between sensor 1 and sensor 8). If the direction of the multiplexed control of the sensor head is in the direction of the gas flow, the various time offsets can be equalized with a corresponding selection of the sensor flow speed, whereby all the corresponding sensor values are obtained at the same time. This is important for the evaluation software to permit processing the increase dynamics of the sensor signals on-line at a seconds timing rate.

Figure 3:
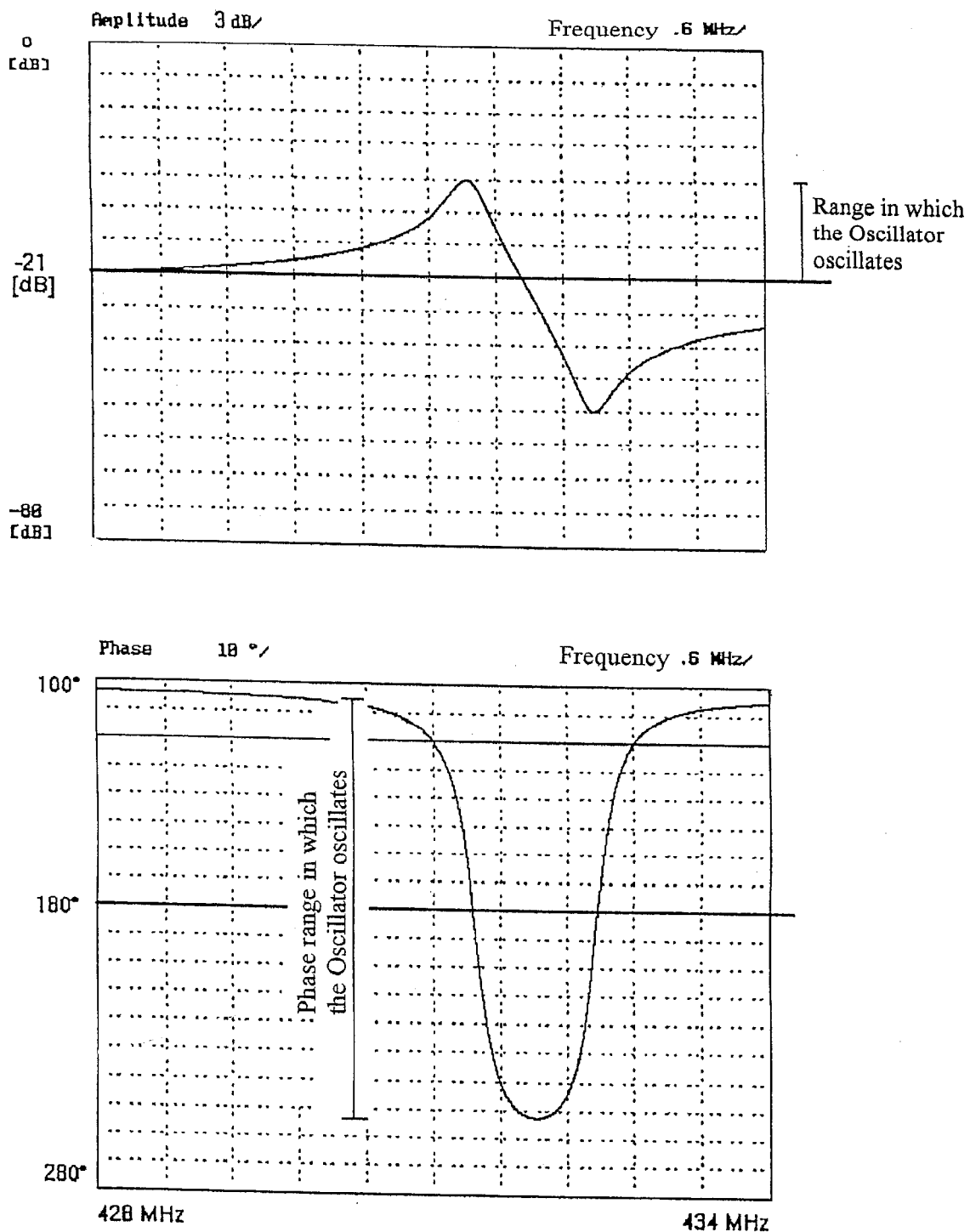
FIG. 3 shows the transmission behavior of a surface acoustic wave building component (SAW).

FIG. 3 shows the typical transmission behavior of the SAW building components used by us. On top, it shows the amplitude range and at the bottom, the phase range based on the frequency.

In order for an oscillator to start oscillating, two conditions must be fulfilled:

1. Amplitude conditions. It means that an oscillator can oscillate only if the amplifier compensates for reduction of the passive building component in the feed back branch.

$$V \text{ amplifier} \times V \text{ passive } BE \geq 1.$$

2. Phase condition: It states that an oscillation develops only when the total phase in the oscillator circuit is $n \times 2\pi$.

$$\phi \text{ amplifier} + \phi \text{ passive } BE = n \times 2\pi \quad n \in = (0, 1, 2, \ldots)$$

The amplifier used by us has an amplification of about 21 dB. This means that with passive building elements with an attenuation of up to −21 dB, it is safely possible to get the oscillator to oscillate.

With the use of an electrically controllable phase shifter in the oscillator circuit, the phase point of the oscillation and, as a result, the oscillation frequency within the transmission curve of the passive building element can be selected. In addition, the oscillator can be so de-tuned that the amplitudes or phase conditions are no longer fulfilled and the oscillation stops.

If one would switch the active component in our oscillator on and off, a strong drift of about 1 . . . 10 kHz/s would be obtained by the power consumption and the heat capacity of the SMD building components upon switching the oscillator on. This drift would worsen our base noise of about 30 Hz by a factor of 30 to 300. By these factors also the detection sensitivities of the sensors would change.

If, however, the active building components remain switched on and the phase in the oscillator circuit is shifted by a phase shifter such that the oscillation stops or restarts, we achieve a correspondingly rapid oscillation start so that, with a measuring time of 1 substitute, it disappears within the base noise (30 Hz). The oscillation re-start and oscillation stopping times for an oscillator switched in this manner is at about 200 µs.

What is claimed is:

1. A sensor comprising a housing, at least two passive building components capable of oscillating together with oscillator circuits disposed in said housing, means for supplying a medium to be examined to said housing and means for removing said medium from said housing, said oscillator circuits each including an amplifier component and a variable phase-shifting component providing for a phase shift range sufficiently large to switch the oscillation of the oscillating components off while said amplifier component remains operative.

2. A sensor according to claim 1, wherein said passive components capable of oscillating are surface acoustic wave building components (SAW).

3. A sensor according to claim 1, wherein said passive components capable of oscillating are oscillation quartzes.

4. A sensor according to claim 1, wherein said passive components capable of oscillating are LC members.

5. A sensor according to claim 1, wherein said variable phase shifting component is an LC low-pass $\pi$ member with capacitance diodes.

6. A sensor according to claim 5, including a circuit for the selective control of the capacitance diodes.

7. A sensor according to claim 1, including a reference oscillator for the downward mixing of the signals.

* * * * *